United States Patent [19]
Jerussi et al.

[11] Patent Number: 4,859,685
[45] Date of Patent: Aug. 22, 1989

[54] ANESTHETIC COMPOSITION AND METHOD OF USING THE SAME

[75] Inventors: Thomas P. Jerussi, Berkeley Heights; John F. Capacchione, Westfield; Mark J. Benvenga, West Orange, all of N.J.

[73] Assignee: BOC, Inc., New Providence, N.J.

[21] Appl. No.: 896,039

[22] Filed: Aug. 13, 1986

[51] Int. Cl.$^4$ ............................................. A61K 31/445
[52] U.S. Cl. ..................................... 514/329; 514/326; 514/818
[58] Field of Search .......................... 514/818, 326, 329

[56] References Cited

U.S. PATENT DOCUMENTS

| | | | |
|---|---|---|---|
| 3,966,934 | 6/1976 | Adams et al. | 514/818 |
| 4,302,465 | 11/1981 | Ekenstam et al. | 514/818 |
| 4,659,714 | 4/1987 | Watt-Smith | 514/818 |

OTHER PUBLICATIONS

Flacke et al, Chem. Abst., vol. 98, #191,500u (1983).
Ghignono et al., Biosis, vol. 80, #105332.
Zimpfer et al, Biosis, vol. 82, #283417.
Malec et al, Chem. Abst., vol. 91, #49486f (1979).

*Primary Examiner*—James H. Reamer
*Attorney, Agent, or Firm*—R. Hain Swope; Larry R. Cassett

[57] ABSTRACT

There is disclosed an injectable anesthetic pharmaceutical composition which does not exhibit muscle rigidity and which includes an anesthetic effective amount of at least one substituted N-(4-piperidinyl)-N-amide and a muscle rigidity inhibiting effective amount of at least one alpha-2 adrenergic agonist as principle ingredients. Also disclosed are methods of inducing and maintaining anesthesia without muscle rigidity by administering said composition to warm blooded animals.

21 Claims, No Drawings

ANESTHETIC COMPOSITION AND METHOD OF USING THE SAME

FIELD OF THE INVENTION

The present invention is directed to an injectable pharmaceutical composition for inducing and maintaining anesthesia without the side-effect of muscle rigidity and methods of using the same.

BACKGROUND OF THE INVENTION

Fentanyl, also known as N-phenyl-N-[1-(2-phenylethyl)-4-piperidinyl] propanamide, and other substituted N-(4-piperidinyl)-N-amides are known in the art as potent analgesics and anesthetics (see, for example, U.S. Pat. Nos. 3,141,823; 3,164,600; 3,998,834; 4,167,574; 4,196,210 and 4,584,303). Such compounds tend to exhibit muscle rigidity in virtually all muscle groups especially chest and abdominal muscles which can interfere with positive pressure ventilation. (See, "*Postoperative Rigidity Following Sufentanil Administration*", Marc Goldberg, M.D. et al., *Anesthesiology*, Vol. 63 No. 2 August, 1985, pp. 199–200; and "*Physiology of Alfentanil-Induced Rigidity*", James L. Benthuysen, M.D. et al., *Anesthesiology*, Vol. 64, 1986, pp. 440–446 and publications cited therein).

Alpha-2 adrenergic agonists are known to decrease the stimulation-induced release of norepinephrine from central and peripheral adrenergic neurons leading to a decrease of sympathetic outflow (e.g., "*Inhibitory Effects of Clondine on Responses to Sympathetic Nerve Stimulation in the Pithed Rat*", J. D. Doxey et al., Br.J.Pharmacol, 61,559 (1977); "*Effects of Clonidine on Central Sympathetic Tone*, H. Klupp et al., Eur.J.Pharmacol. 10, 225 (1970); and "*Centrally Mediated Decrease in Sympathetic Tone Induced by 2(2,6-dichlorophenylamino)-2 imidazoline*", H. Schmitt et al., Eur.J.Pharmacol. 1, 147 (1967)). Such compounds are also known to have vasopressor and antihypertensive activity and include clonidine and derivatives thereof (U.S. Pat. Nos. 3,202,660 and 3,454,701) guanfacine and derivatives thereof (U.S. Pat. No. 3,632,645), guanabenz (U.K. Patent No. 1,019,120) and alpha-methyl DOPA (U.S. Pat. No. 3,230,143).

Applicants have discovered that the administration of an injectable pharmaceutical composition containing the above-mentioned substituted N-(4-piperidinyl)-N-amides (e.g., fentanyl) and alpha-2-adrenergic agonists (e.g., clonidine) provides the same desirable anesthetic effect but substantially eliminates the muscle rigidity associated with the administration of compositions containing the substituted amides alone. Furthermore, the present pharmaceutical composition reduces the amount of anesthetic needed to induce anesthesia by as much as seven times and also reduces the amount of inhalation anesthetic often used to maintain anesthesia. Still further the present composition stablizes cardiovascular parameters during anesthesia.

It is therefore an object of the present invention to provide an injectable pharmaceutical anesthetic composition that substantially eliminates the side-effect of muscle rigidity.

It is another object of the invention to provide an injectable pharmaceutical composition wherein a reduced amount of substituted N-(4-piperidinyl)N-amide is needed to achieve the onset of anesthesia.

It is another object of the invention to provide an injectable pharmaceutical composition which reduces the amount of inhalation anesthetic used to maintain anesthesia.

It is another object of the invention to provide an injectable pharmaceutical anesthetic composition which maintains stabilized cardiovascular parameters.

It is another object of the invention to provide a method of anesthetizing warm blooded animals without the side effect of muscle rigidity.

SUMMARY OF THE INVENTION

The present invention is directed to an injectable pharmaceutical composition for inducing and maintaining anesthesia without muscle rigidity comprising:

(a) an anesthetic effective amount of at least one substituted N-(4-piperidinyl)-N-amide or pharmaceutically acceptable acid addition salts thereof;

(b) a muscle rigidity inhibiting effective amount of at least one alpha-2 adrenergic agonist or pharmaceutically acceptable acid addition salts thereof; and (c) a pharmaceutically acceptable carrier.

The present invention is also directed to methods of inducing and maintaining anesthesia without muscle rigidity by injection of the composition into warm blooded animals.

The substituted N-(4-piperidinyl)-N-amides employed in the present invention include fentanyl, i.e., N-phenyl-N-[1-(2-phenylethyl)-4-piperidinyl] propanamide and derivatives thereof which have potent analgesic properties making them useful as anesthetics. Fentanyl and methods of preparing the same are disclosed in U.S. Pat. Nos. 3,141,823 and 3,164,600 each of which is incorporated herein by reference.

Other fentanyl-like compounds having potent analgesic and anesthetic properties include, for example, compounds having the formula:

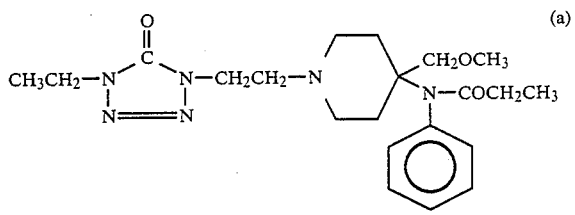

(a)

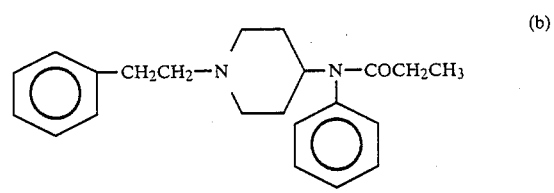

(b)

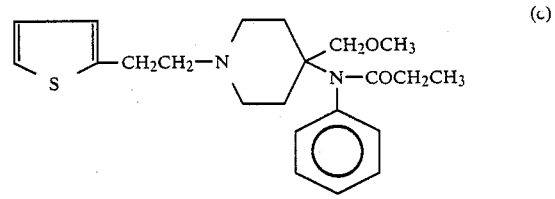

(c)

-continued

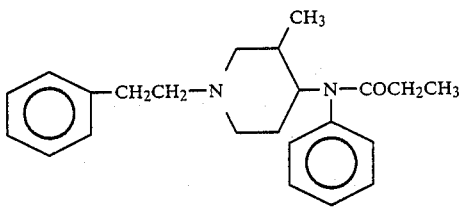 (d)

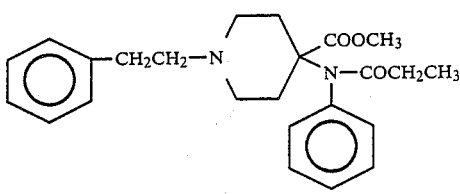 (e)

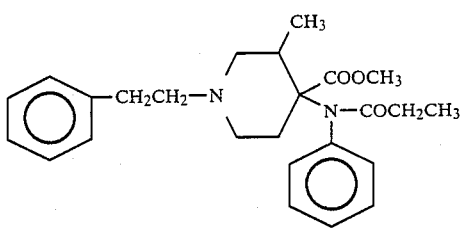 (f)

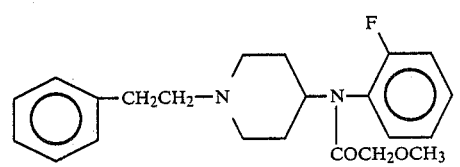 (g)

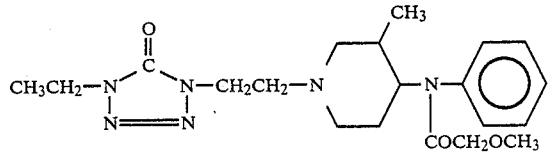 (h)

or pharameutically acceptable salts thereof. Such compounds are disclosed in U.S. Pat. Nos. 3,998,834; 4,167,574; 4,196,210 and 4,584,303 incorporated herein by reference which also disclose methods of making such compounds.

The alpha-2-adrenergic agonists which may be employed in the present invention in combination with fentanyl and related compounds include guanabenz, alpha-methyl DOPA, compounds of the formula

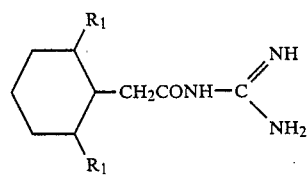

wherein $R_1$ is chlorine or methyl, and substituted 2-(phenylamino)-1,3-diazacyclopentenes-(2) having the formula:

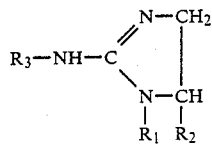

wherein $R_1$ and $R_2$ are each independently selected from the group consisting of hydrogen, methyl and ethyl and $R_3$ is selected from the group consisting of trifluoromethyl-phenyl; 2,6-dichloro-phenyl; 2-chloro-6-methyl-phenyl; 2-methyl-4-chloro-phenyl; 2-chloro-4-methyl-phenyl; 2-chloro-4-ethyl-phenyl; 2-chloro-6-ethyl-phenyl; 2-chloro-4-tert.butyl-phenyl; 2,6-dichloro-4-methyl-phenyl; 2,4-dichloro-6-methyl-phenyl; 2,4-dimethyl-6-chloro-phenyl; 2,6-dimethyl-4-chloro-phenyl; and their pharmaceutically acceptable acid addition salts. All such compounds and method of making the same, except guanabenz, are disclosed in U.S. Pat. Nos. 3,632,645; 3,230,143; 3,202,660; and 3,454,701 respectively, each of which is incorporated herein by reference.

Guanabenz may be prepared by reacting a compound of the formula

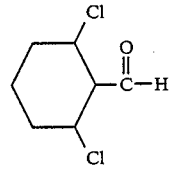

with a compound of the formula

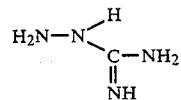

in the presence of a suitable solvent such as, for example, ethylalcohol/benzene at a temperature of between 50° and 100° C. with or in the absence of a catalyst such as p-toluenesulfonic acid (about 1% by weight based on the weight of the latter compound mentioned above). If desired, the reactants may be refluxed with the continuous removal of water. The desired compound may be isolated from the reaction mixture in a conventional manner, for example, by distilling off the solvent and purifying the residue by distillation, crystallization or chromatography, as disclosed in U.S. Pat. No. 3,982,020 incorporated herein by reference.

Alternatively, guanabenz may be prepared from 2,6-dichlorobenzaldehyde and aminoguanidine bicarbonate and HCl in butanol as disclosed in U.S. Pat. No. 3,975,533 incorporated herein by reference.

The free base compounds employed in the composition of the present invention may be transformed into pharmaceutically acceptable acid addition salts by customary methods described in the aforementioned patents as, for example, by acidifying a solution of the free base in a suitable organic solvent with the desired acid. Such acids may be inorganic and organic and include by way of example sulfuric, phosphoric, hydrochloric, hydrobromic, hydroiodic, sulfamic, citric, lactic, maleic, malic, succinic, tartaric, cinnamic, acetic, benzoic, gluconic, ascorbic and related acids. The compounds may also form quaternary ammonium salts with a variety of organic esters of sulfuric, hydrohalic and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethylsulfate, diethylsulfate, methyl benzenesulfonate, ethyltoluenesulfonate, ethylene chlorohydrin, propylene chlorohydrin, allyl bromide, methallyl bromide and crotyl bromide.

Compositions of the present invention may be made, for example, by preparing separate stock solutions containing the respective active ingredients and a pharmaceutically acceptable carrier such as distilled water to provide a concentration of the active ingredient in each of the stock solutions of about 1.0 mg./ml. The stock solutions are then combined to form an injectable solution in a manner such that the concentration of the active ingredients in the injectable composition is in the range of from about 0.001 to about 1.0 mg/kg, preferably from about 0.01 to about 0.20 mg/kg for the substituted amide and from about 0.001 to about 1.0 mg/kg, preferably from about .001 to about .020 mg/kg for the alpha-2-adrenergic agonist.

The compositions of the present invention may be administered to warm blooded animals including humans in any manner by injection, preferably intravenously.

Pharmaceutically acceptable carriers which may be employed to make the composition include, in addition to distilled water, saline and other customarily employed aqueous carriers.

The following examples are for illustrative purposes only and are not meant to limit the invention encompassed by the claims forming part of the present application.

EXAMPLES 1-3

The following are definitions of terms used in this example and those that follow:

"Loss of Righting" (LOR)—is a general measure of the onset of anesthesia and specifically "righting" is lost when the test animal remains supine for at least 30 seconds.

"Analgesia"—is achieved when a supramaximal paw pinch is delivered to the test animal with a pair of Kelly forceps and there is no vocalization or overt movement in response thereto.

"Muscle Rigidity"—is indicated by extreme extensor muscle tone and the absence of hind limb flexion while standing the stiff test animal in a supported vertical postion. The degree of rigidity is visually determined on a scale of 0 (no rigidity) to 3 (extreme rigidity).

Three samples of the present composition (Samples 1-3) were prepared by combining 1 mg/ml solutions of fentanyl and clonidine in distilled water, respectively so that the respective combined solutions had the concentrations shown in Table 1. Each of the combined solutions were injected as a bolus into a tail vein of a restrained Male Sprague-Dawley rat. After injection, the rat was removed from the restrainer and observed for twenty minutes.

Measurements were taken during the observation period to determine the percent loss of righting, the percent of analgesia and the degree of muscle rigidity. The results are shown in Table 1.

The results were compared with control compositions containing the amounts of clonidine or fentanyl alone as shown in Table 1 which were administered to comparable rats in the same manner as Samples 1-3. The results are shown in Table 1.

TABLE 1

| Sample* | Clonidine Amount (mg/kg) | Fentanyl Amount (mg/kg) | LOR (%) | LOR Duration (minutes) | Analgesia (%) | Analgesia Duration (minutes) | Rigidity |
|---|---|---|---|---|---|---|---|
| 1 | 0.002 | 0.005 | 0 | — | 0 | — | 0.0 |
| 2 | 0.005 | 0.005 | 33 | 0.7 | 0 | — | 0.0 |
| 3 | 0.010 | 0.005 | 100 | 2.6 | 0 | — | 0.0 |
| Control | 0.035 | 0.0 | 0 | — | 0 | — | 0.0 |
| Control | 0.0 | 0.010 | 0 | — | 33 | 3.0 | 0.3** |
| Control | 0.0 | 0.020 | 67 | 3.7 | 100 | 8.8 | 1.6** |
| Control | 0.0 | 0.025 | 83 | 6.4 | 100 | 14.1 | 2.0** |
| Control | 0.0 | 0.035 | 100 | 8.8 | 100 | 13.5 | 2.5** |

*The number of test animals receiving doses of clonidine alone or the combination of fentanyl and clonidine was 3. The number of test animals receiving fentanyl alone was 6. All data listed in Table 1 is an average for the number of treated test animals.
**Rigidity lasted the entire period of LOR Duration.

As shown by the control samples in Table 1, muscle rigidity becomes extreme as the dose of fentanyl increases to an effective anesthesia level (100% LOR) in the absence of clonidine. In contradistinction, the combination of clonidine and fentanyl at the 100% LOR level results in no muscle rigidity. Furthermore, the amount of fentanyl necessary to achieve a 100% LOR level employing the composition of the present invention is one-seventh the amount (0.005 mg/kg vs. 0.035 mg/kg) needed to obtain the same anesthesia induced state when fentanyl is administered alone.

EXAMPLES 4-6

Three samples of the composition of the present invention (Samples 4-6) having the amounts of fentanyl and clonidine shown in Table 2 were prepared by the method described in Example 1. The results are shown in Table 2.

TABLE 2

| Sample* | Clonidine Amount (mg/kg) | Fentanyl Amount (mg/kg) | LOR (%) | LOR Duration (minutes) | Analgesia (%) | Analgesia Duration (minutes) | Rigidity |
|---|---|---|---|---|---|---|---|
| 4 | 0.005 | 0.002 | 0 | — | 0 | — | 0.0 |
| 5 | 0.005 | 0.005 | 33 | 0.7 | 0 | — | 0.0 |

TABLE 2-continued

| Sample* | Clonidine Amount (mg/kg) | Fentanyl Amount (mg/kg) | LOR (%) | LOR Duration (minutes) | Analgesia (%) | Analgesia Duration (minutes) | Rigidity |
|---|---|---|---|---|---|---|---|
| 6 | 0.005 | 0.010 | 100 | 2.3 | 100 | 2.5 | 1.0** |

*Each composition was administered to three test animals and the results are an average of the treated test animals.
**Rigidity lasted less than one minute.

As can be seen from the results in Table 2 an effective state of anesthesia was obtained by administering the composition of the present invention containing only 0.010 mg/kg of fentanyl (Sample 6) as compared to 0.035 mg/kg of fentanyl (see Table 1) when used alone. In addition, only mild, transient muscle rigidity was observed at the effective dose for the combination of fentanyl and clonidine while muscle rigidity experienced by the administration of fentanyl alone was extreme and prolonged as shown in Table 1.

EXAMPLES 7-12

Six samples of the present composition (Samples 7-12) having the dosages amounts listed in Table 3 were prepared and administered in the same manner as described in Example 1. The results are shown in Table 3.

TABLE 3

| Sample* | Clonidine Amount (mg/kg) | Fentanyl Amount (mg/kg) | LOR (%) | LOR Duration (minutes) | Analgesia (%) | Analgesia Duration (minutes) | Rigidity |
|---|---|---|---|---|---|---|---|
| 7 | 0.002 | 0.002 | 0 | — | 0 | — | 0.0 |
| 8 | 0.005 | 0.005 | 33 | 0.7 | 0 | — | 0.0 |
| 9 | 0.010 | 0.010 | 100 | 3.2 | 66 | 4.8 | 0.6** |
| 10 | 0.020 | 0.020 | 100 | 10.2 | 100 | 9.7 | 1.3** |
| 11 | 0.025 | 0.025 | 100 | >17.2 | 100 | 14.9 | 1.0** |
| 12 | 0.035 | 0.035 | 100 | >18.6 | 100 | >19.4 | 1.0** |

*Each composition was administered to three test animals. The results are an average of the treated test animals.
**Rigidity lasted less than one minute.

As shown in Table 3, equal doses of clonidine and fentanyl in a composition of the present invention achieved the desired anesthetic effect with as little as 0.010 mg/kg of fentanyl as compared with 0.035 mg/kg using fentanyl alone (see Table 1). Furthermore, consistent with the results obtained from samples 4-6 as shown in Table 2, the addition of clonidine to fentanyl resulted in only mild, transient muscle rigidity as compared with extreme and prolonged muscle rigidity evidenced in the test animals receiving fentanyl alone.

We claim:

1. An injectable pharmaceutical composition for inducing and maintaining anesthesia without muscle rigidity comprising:
   (A) an anesthetic effective amount of at least one substituted N-(4-piperidinyl)-N-amide selected from the group consisting of

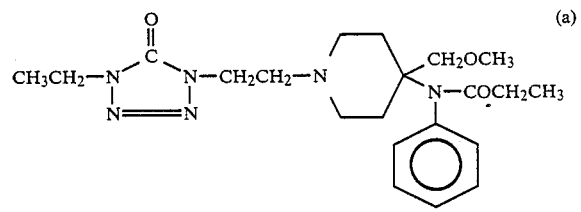
(a)

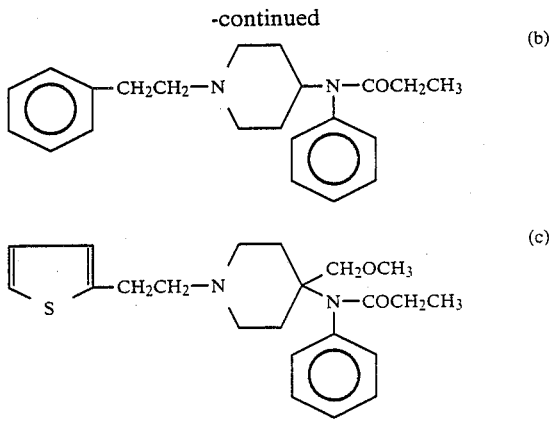
(b)

(c)

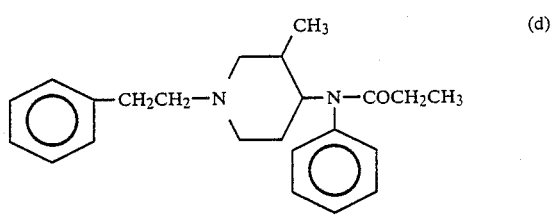
(d)

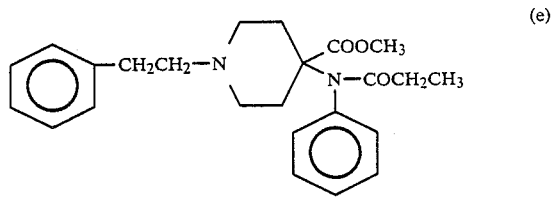
(e)

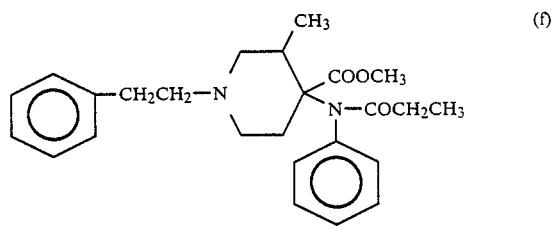
(f)

-continued

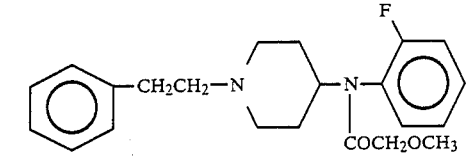

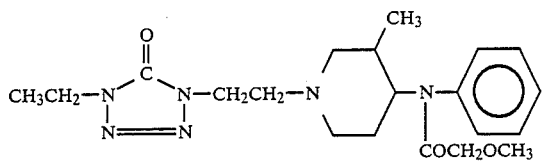

or pharmaceutically acceptable salts thereof.

(B) a muscle rigidity inhibiting effective amount of at least one alpha-2 adrenergic agonist selected from the group consisting of guanabenz alpha-methyl DOPA, compounds of the formula

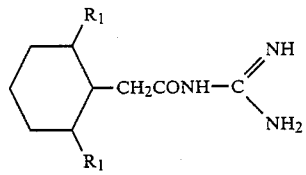

wherein $R_1$ is chlorine or methyl, and substituted 2-(phenylamino)-1,3-diazacyclopentenes-(2) having the formula

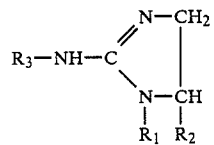

wherein $R_1$ and $R_2$ are each independently selected from the group consisting of hydrogen, methyl and ethyl and $R_3$ is selected from the group consisting of trifluoromethyl-phenyl; 2,6-dichloro-phenyl; 2-chloro-6-methyl-phenyl; 2-methyl-4-chloro-phenyl; 2-chloro-4-methyl-phenyl; 2-chloro-4-ethyl-phenyl; 2-chloro-6-ethyl-phenyl; 2-chloro-4-tert. butyl-phenyl; 2,6-dichloro-4-methyl-phenyl; 2,4-dichloro-6-methyl-phenyl; 2-4-dimethyl-6-chlorophenyl; 2,6-dimethyl-4-chloro-phenyl; and pharmaceutically acceptable acid addition salts thereof; and (C) a pharmaceutically acceptable carrier.

2. The composition of claim 1 wherein $R_1$ and $R_2$ are each hydrogen and $R_3$ is 2,6-dichloro-phenyl.

3. The composition of claim 1 wherein the substituted N-(4-piperidinyl)-N-amide is a compound of the formula:

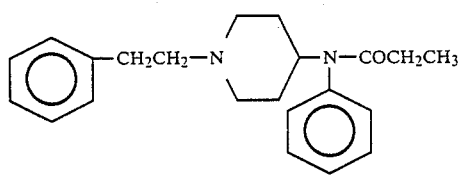

or pharmaceutically acceptable salts thereof.

4. The composition of claim 1 wherein the anesthetic effective amount of the substituted N-(4-piperidinyl)-N-amide is in the range of from about 0.001 mg/kg to about 1.0 mg/kg.

5. The composition of claim 4 wherein the anesthetic effective amount of the substituted N-(4-piperdinyl)-N-amide is in the range from about 0.01 to about 0.20 mg/kg.

6. The composition of claim 1 wherein the muscle rigidity inhibiting effective amount of the alpha-2 adrenergic agonist is in the range of from about 0.001 mg/kg to about 1.0 mg/kg.

7. The composition of claim 6 wherein the muscle rigidity inhibiting effective amount of the alpha-2-adrenergic agonist is in the range of from about 0.001–0.020 mg/kg.

8. An injectable pharmaceutical composition for inducing and maintaining anesthesia without muscle rigidity consisting essentially of:

(a) an anesthetic effective amount of a compound of the formula:

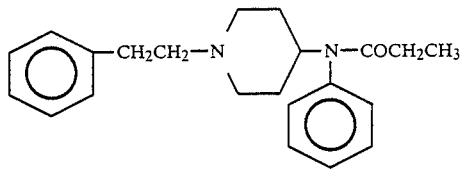

or pharmaceutically acceptable salts thereof;

(b) a muscle rigidity inhibiting effective amount of a compound of the formula:

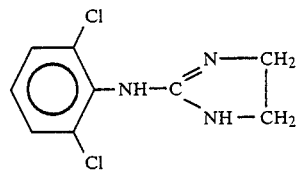

or pharmaceutically acceptable acid addition salts thereof; and (c) a pharmaceutically acceptable carrier.

9. The composition of claim 8 wherein the anesthetic effective amount of compound (a) is from about 0.001 mg/kg to about 1.0 mg/kg and the muscle rigidity inhibiting amount of compound (b) is from about 0.001 mg/kg to about 1.0 mg/kg.

10. The composition of claim 9 wherein the anesthetic effective amount of compound (a) is from about 0.01 to about 0.20 mg/kg and the muscle rigidity inhibiting effective amount of compound (b) is from about .001 to about 0.020 mg/kg.

11. A method of inducing and maintaining anesthesia without muscle rigidity in a warm blooded animal comprising administering to said warm blooded animal an effective amount of an injectable pharmaceutical composition comprising:

(A) an anesthetic effective amount of at least one substituted N-(4-piperidinyl)-N-amide selected from the group consisting of:

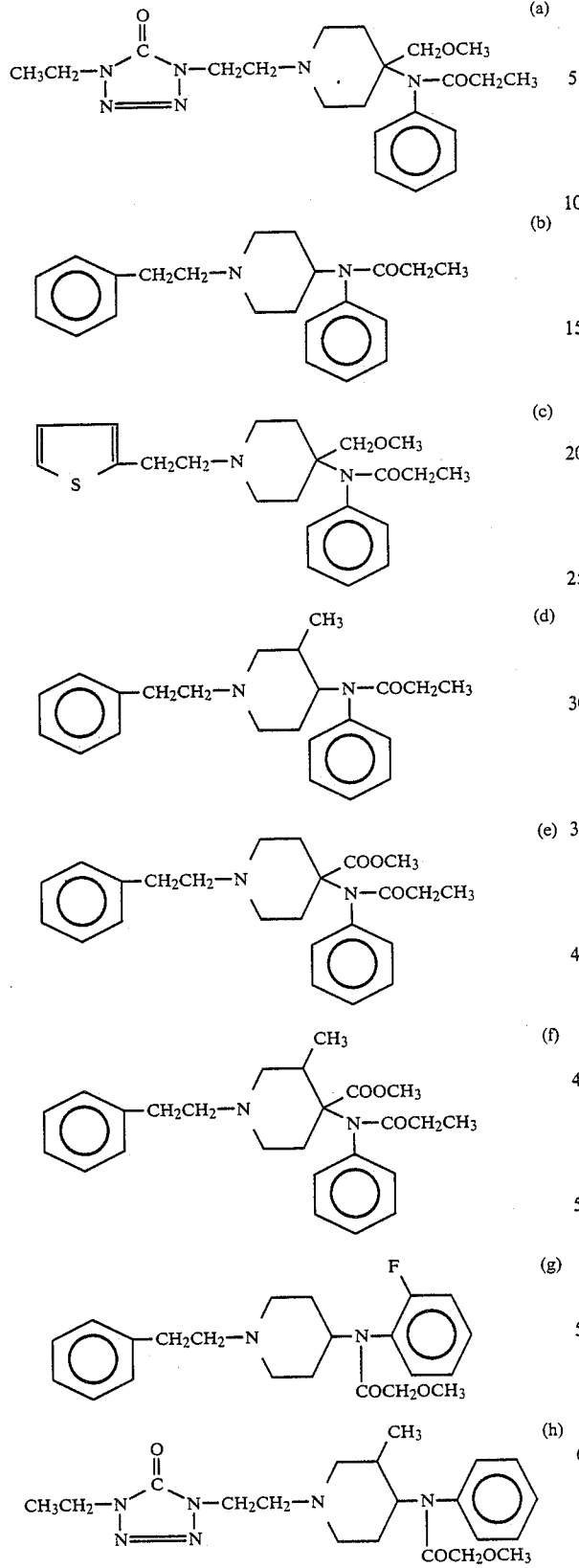

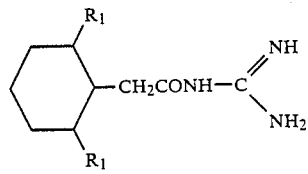

and pharmaceutically acceptable salts thereof;

(B) a muscle rigidity inhibiting effective amount of at least one alpha-2 adrenergic agonist selected from the group consisting of guanabenz alpha-methyl DOPA, compounds of the formula:

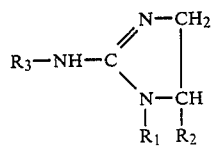

wherein $R_1$ is chlorine or methyl and substituted 2-(phenylamino)-1,3-diazacyclopentenes-(2) having the formula:

$$R_3-NH-C \underset{\underset{R_1}{N}-\underset{R_2}{CH}}{\overset{N-CH_2}{=}}$$

wherein $R_1$ and $R_2$ are each independently selected from the group consisting of hydrogen, methyl and ethyl and $R_3$ is selected from the group consisting of trifluoro-methyl-phenyl; 2-6-dichloro-phenyl; 2-chloro-6-methyl-phenyl; 2-methyl-4-chloro-phenyl; 2-chloro-4-methyl-phenyl; 2-chloro-4-ethyl-phenyl; 2-chloro-6-ethyl-phenyl; 2-chloro-4-tert. butyl-phenyl; 2,6-dichloro-4-methyl-phenyl; 2,4-dichloro-6-methyl-phenyl; 2,4-dimethyl-6-chloro-phenyl; 2,6-dimethyl-4-chloro-phenyl; and pharmaceutically acceptable acid addition salts thereof; and (C) a pharmaceutically acceptable carrier.

12. The method of claim 1 wherein $R_1$ and $R_2$ are each hydrogen and $R_3$ is 2,6-dichloro-phenyl.

13. The method of claim 11 comprising administering the composition intravenously to the warm blooded animal.

14. The method of claim 11 wherein the substituted N-(4-piperidinyl)-N-amide is a compound of the formula:

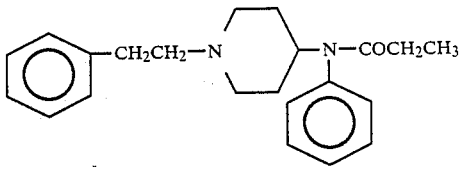

or pharmaceutically acceptable salts thereof.

15. The method of claim 11 wherein the anesthetic effective amount of the substituted N-(4-piperidinyl)-N-amide is in the range of from about 0.001 mg/kg to about 1.0 mg/kg.

16. The method of claim 15 wherein the anesthetic effective amount of the substituted N-(4-piperidinyl)-N-amide is in the range of from about 0.01 mg/kg to about 0.20 mg/kg.

17. The method of claim 11 wherein the muscle rigidity inhibiting effective amount of the alpha-2 adrenergic agonist is in the range of from about 0.001 mg/kg to about 1.0 mg/kg.

18. The method of claim 17 wherein the muscle rigidity inhibiting effective amount of the alpha-2 adrenergic agonist is in the range of from about 0.001 mg/kg to about 0.020 mg/kg.

19. The method of claim 11 wherein said composition consists essentially of:
(a) an anesthetic effective amount of a compound of the formula

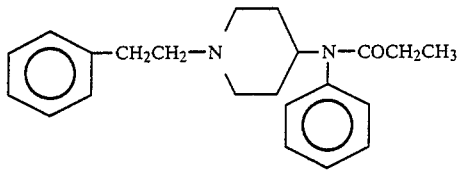

or pharmaceutically acceptable salts thereof.
(b) a muscle rigidity inhibiting effective amount of a compound of the formula

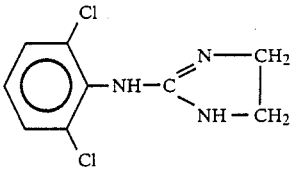

or pharmaceutially acceptable acid addition salts thereof; and
(c) a pharmaceutically acceptable carrier.

20. The method of claim 19 wherein the anesthetic effective amount is from about 0.001 mg/kg to about 1.0 mg/kg and the muscle rigidity inhibiting amount is from about 0.001 mg/kg to about 1.0 mg/kg.

21. The method of claim 20 wherein the composition is administered by intravenous injection to a warm blooded animal.

* * * * *